US012616486B2

(12) United States Patent　(10) Patent No.:　US 12,616,486 B2
Gautier et al.　(45) Date of Patent:　May 5, 2026

(54) SYSTEMS, METHODS, AND APPARATUSES FOR TIBIAL MECHANICAL AXIS DIGITIZATION

(71) Applicant: ORTHOSOFT ULC, Montreal (CA)

(72) Inventors: Manon Gautier, Montreal (CA);
Elaine Huang, Montreal (CA);
Martine Blouin, Montreal (CA);
Joseph Madier Vigneux, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 199 days.

(21) Appl. No.: 18/508,691

(22) Filed: Nov. 14, 2023

(65) Prior Publication Data

US 2024/0156472 A1　May 16, 2024

Related U.S. Application Data

(60) Provisional application No. 63/425,002, filed on Nov. 14, 2022.

(51) Int. Cl.
*A61B 17/17*　(2006.01)
*A61B 17/15*　(2006.01)
*A61B 17/00*　(2006.01)

(52) U.S. Cl.
CPC ........ *A61B 17/1764* (2013.01); *A61B 17/157* (2013.01); *A61B 2017/00455* (2013.01)

(58) Field of Classification Search
CPC .. A61B 17/1764; A61B 17/164; A61B 17/157
See application file for complete search history.

(56) References Cited

U.S. PATENT DOCUMENTS

| | | | |
|---|---|---|---|
| 2012/0245589 A1 | 9/2012 | Fisher et al. | |
| 2014/0276000 A1* | 9/2014 | Mullaney | A61B 34/20 600/424 |
| 2015/0342516 A1 | 12/2015 | Nguyen et al. | |
| 2018/0296232 A1* | 10/2018 | Nielsen | A61B 17/155 |

FOREIGN PATENT DOCUMENTS

KR　10-2019-0022578 A　3/2019

* cited by examiner

*Primary Examiner* — Andrew Yang
(74) *Attorney, Agent, or Firm* — NORTON ROSE FULBRIGHT CANADA LLP

(57) ABSTRACT

A system may include an implantable device having at least a first sensor configured to collect first data regarding one or more characteristics of a bone of a patient, wherein the implantable device is configured for implantation in a medullary canal of the tibia. The system may include an attachment member configured to couple with the implantable device when the implantable device is implanted in the medullary canal of the tibia. The system may further include a targeting device moveably coupled to the attachment member, wherein the targeting device is configured to reference a distal anatomy of a leg, and wherein the targeting device has at least a second sensor configured to collect second data regarding at least a position of the targeting device.

14 Claims, 7 Drawing Sheets

SYSTEMS, METHODS, AND APPARATUSES FOR TIBIAL MECHANICAL AXIS DIGITIZATION

CROSS-REFERENCE TO RELATED APPLICATION

The present application claims the priority of U.S. patent application No. 63/425,002, filed on Nov. 14, 2022 and incorporated herein by reference.

TECHNICAL FIELD

The present disclosure is directed to systems, devices and methods for computer-assisted surgery, such as in arthroplasty procedures.

BACKGROUND

Arthroplasty procedures involve the use of specialized tools and the implantation of medical devices such as orthopedic implants, into a patient. These orthopedic implants can replicate one or more portions of a joint from which bone has been removed. Typically, once the orthopedic implant is implanted into the patient, or even while it is being implanted, it is difficult to obtain feedback regarding the effectiveness of the implant or the implant procedure. Attempts have been made to obtain data from orthopedic implants using sensors. Efforts in this area are still being actively pursued and refined. However, such "smart" orthopedic implants can be costly, may require redesigns, and can suffer from incomplete sensor data, short battery life, and infrequent data collection.

Computer-assisted surgery (CAS) systems such as those that employ inertial-based or microelectro-mechanical sensor (MEMS), trackable members have been developed. One of the principal steps in navigating a bone with inertial sensors is to determine a coordinate system of the bone relative to the sensors, so as to be able to track the orientation of the bone. However, bone axis digitizer devices that support MEMS typically must have multi-point attachments to eliminate movement, may be bulky, and can experience accidental displacement during surgery.

OVERVIEW

The present subject matter can provide a solution to these and other problems, such as by providing a CAS system that can better accommodate and track orientation and any movement of a bone such as the tibia. This CAS system can utilize a dedicated smart implant (called an implantable device herein) with sensing capability in combination with other system components including a second one or more sensors and a laser assembly to more accurately digitize a mechanical axis of the tibia. The present CAS system also reduces a likelihood of human error, which could result from accidental displacement of sensor(s) during surgery.

The disclosed CAS system contemplates that the implantable device can be configured to be coupled to the anatomy and further can be coupled to one or more of the tool(s) to provide a reference from which the tool(s) can be oriented. It is advantageous that the implantable device can be configured to be inserted into the medullary canal, which approximates a position of the mechanical axis of the tibia. Thus, various other tools of the CAS system can reference the implantable device and other anatomy of the patient as discussed further herein.

One contemplated use of the CAS systems, methods and apparatuses disclosed herein is during trialing. During a surgical arthroplasty procedure to implant a prosthetic knee joint, trialing involves performing range of motion and other determinations, use of tools such as cut guides to remove diseased bone from the joint and the use of one or more provisional components to obtain proper sizing for permanent orthopedic implants.

DETAILED DESCRIPTION

CAS has been developed in order to help a surgeon to alter bones, and to position or orient implants to a desired location. CAS may encompass a wide range of devices, including surgical navigation, pre-operative planning, trialing and various robotic devices. Many conventional techniques of joint arthroplasties do not use a robot, which can result in errors or can lack precision. CAS systems can help to reduce errors and increase precision. CAS can be improved by making a better determination of a location/orientation of bone(s) and instruments as it relates to the bone(s). This improvement can help improve accuracy of positioning for cutting operations performed, in part or in whole, by the CAS system. However, existing tracking devices of CAS can be improved. This disclosure provides for improvements with respect to digitizing the mechanical axis of the bone, bone tracking and other sensing of patient characteristics.

The smart implants, methods and systems described herein can be used as part of a CAS system such as an inertial-based CAS system employing trackable members having inertial-based sensors. The inertial-based CAS system can utilize sensors such as the micro-electromechanical sensors (MEMS) based system and methods disclosed in co-pending U.S. Provisional patent applications IMPLANTABLE SENSOR FOR DETERMINING ORIENTATION AND MOVEMENT OF BONE and COMPUTER-ASSISTED TIBIA RESECTION filed on the even day with the present case and disclosed in U.S. Pat. Nos. 10,874,405, 10,729,452, 9,901,405, 9,839,533 and 8,265,790, the entire contents of each of which are incorporated herein in its entirety by reference. However, it is to be understood that the implantable devices, methods and systems described herein may also be used with other computer-assisted surgery (CAS) systems such as those using Rosa® Robotic Technology and/or with other tracking modalities, such as optical tracking. It is further contemplated that the implantable devices, although described herein as temporary implants used during trialing, could be utilized as permanent implant to provide postoperative sensing capability after implantation of traditional orthopedic implants. The term "bone" as used herein is not limited to the tibia but can include any applicable bone of the body including the humerus, femur, fibula, foot, etc. Although the examples are described herein in reference to mounting of the implantable device in the medullary canal of the tibia and reference a knee arthroplasty, the apparatuses, systems, techniques and methods discussed herein are not so limited and can be used in other anatomic locations such as adjacent other joints such as the spine, shoulder, hip, ankle, wrist or the like.

Figure 1:
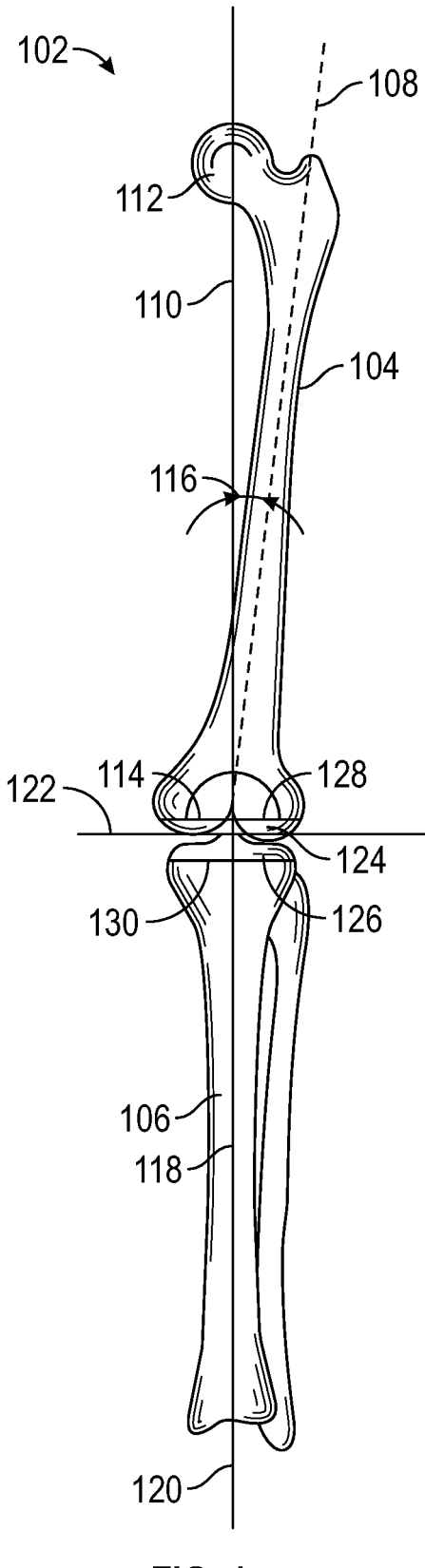
FIG. 1 illustrates knee joint structures providing suitable environments in which the CAS system in accordance with an example of the present application can be utilized.

FIG. 1 illustrates several features of knee joint structures. In FIG. 1, a frontal view of a lower leg 102, including a femur 104 and a tibia 106, is shown to illustrate various lower limb axes. The femur 104 has an anatomic axis 108 that coincides generally with its intramedullary canal. The femur 104 also has a mechanical axis 110, or load axis, running from the center of a femoral head 112 to the center of a knee joint 114. The angle 116 extending between these two axes varies among the patient population, but is generally on the order of between 5-7 degrees, inclusive. Like the femur 104, the tibia 106 also has an anatomic axis coinciding generally with its intramedullary canal. The mechanical axis 118 of the tibia 106 runs from the center of the knee joint 114 to the center of an ankle region 120 (middle of the malleoli) and is generally collinear with its anatomic axis.

A joint line 122, about which the knee joint 114 flexes, is approximately parallel to a line through medial and lateral femoral condyles 124 and to a tibial plateau 126. Although illustrated as perpendicular in FIG. 1, the joint line 122 can extend at a varus or valgus angle relative to the mechanical axes 110 and 118 of the femur 104 and tibia 106, respectively. Normally, during a partial or total knee replacement procedure, portions of a distal end of the femur 104 or a proximal end of the tibia 106 are resected to be parallel or approximately parallel to the joint line 122, and thus perpendicular to the mechanical axes 110 and 118, as indicated at 128 and 130, respectively.

As used herein, "proximal" refers to a direction generally toward the torso of a patient, and "distal" refers to the opposite direction of proximal, i.e., away from the torso of a patient. "Anterior" refers to a direction generally toward the front of the patient, and "posterior" refers to the opposite direction of anterior, i.e., toward the rear of the patient. The term "anterior-posterior" can be anterior to posterior or posterior to anterior. The term "proximal-distal" can be proximal to distal or distal to proximal. The term "medial-lateral" can be lateral to medial or medial to lateral.

Figure 2:
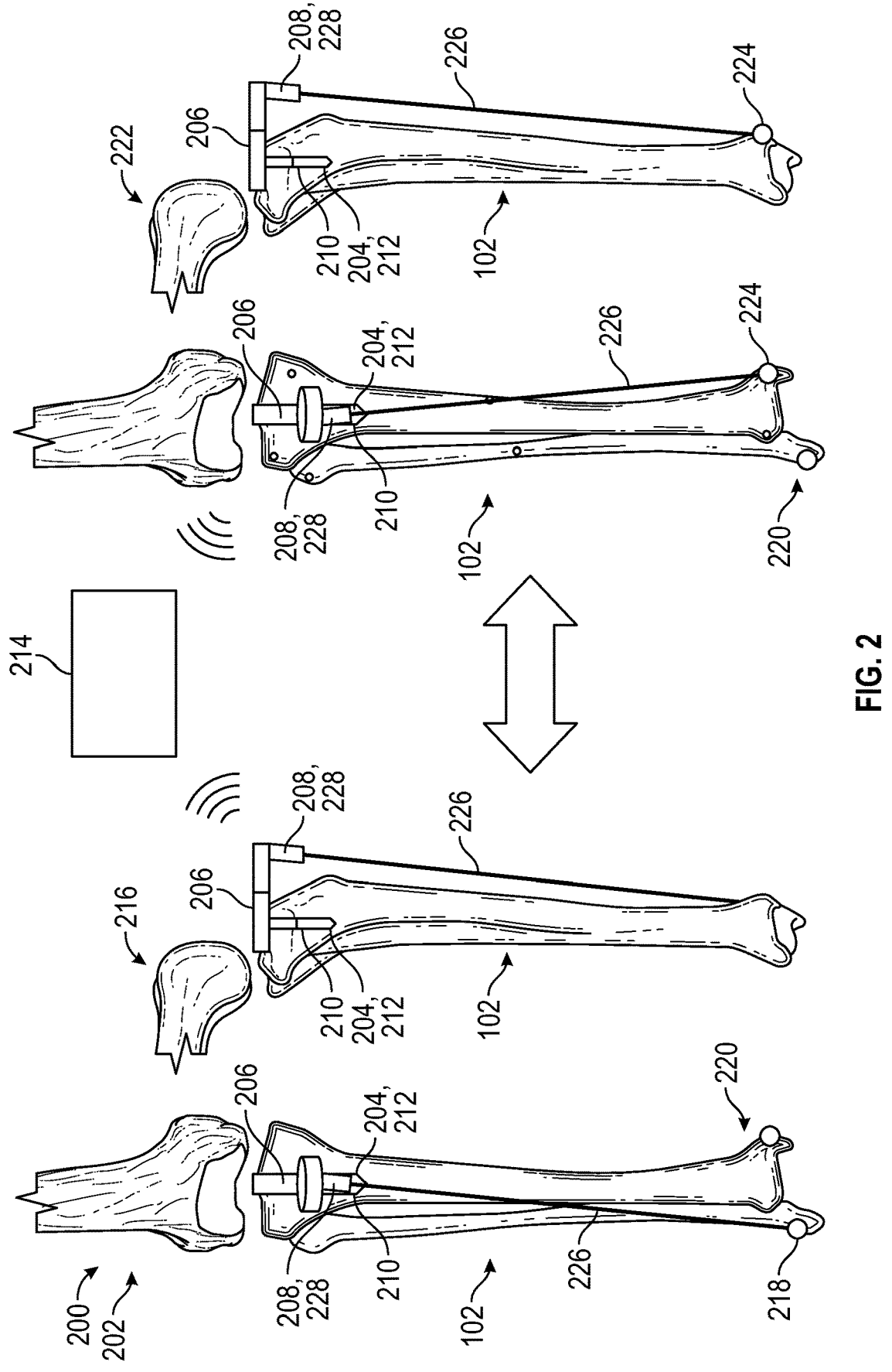
FIG. 2 shows a method and system of digitizing a mechanical axis of a tibia using a targeting device producing a laser beam and an implantable device having a sensor positioned in a medullary canal of the tibia in accordance with an example of the present application.

FIG. 2 shows a system 200 and a method 202 used according to techniques of the present application to digitize the mechanical axis 118 (FIG. 1) of the tibia 106. The system 200 can include an implantable device 204, an attachment mechanism 206 and a targeting device 208. The method 202 shows the system 200 being used to identify one or more locations on a distal anatomy of the leg 102.

FIG. 2 shows the tibia 106 and the femur 104 in both an anterior side view and a medial side view. As shown in FIG. 2, the implantable device 204 can be implanted into a medullary canal 210 of the tibia 106. The implantable device 204 can include one or more onboard electronics including one or more sensors 212. The system 200 can include one or more electronic device(s) external of the patient. These one or more electronic device(s) are referenced herein as a controller 214 for simplicity.

The controller 214 can intraoperatively receive first data from the implantable device 204. This first data can include, but is not limited to, information about a position of the implantable device 204, which approximates the position of the medullary canal 210. The medullary canal 210 is located along the mechanical axis of the tibia 106. Thus, a first position of the mechanical axis can be determined from the first data. The one or more sensors 212 can also collect further data regarding angulation, movement, temperature, pH, etc. of the tibia 106. Thus, the one or more sensors 212 can include any one or combination of different types of sensors (e.g., an accelerometer, a gyroscope, a compass, an electronic tilt sensor, a piezoelectric sensor, force sensor, thermometer, pH monitor, strain gauge, or any combination or multiples thereof, including any other sensor that can be used to detect position and/or motion within a body).

The attachment mechanism 206 can be configured to couple with the implantable device 204 within the medullary canal 210. The attachment mechanism 206 can additionally be configured to couple with the targeting device 208. Thus, the attachment mechanism 206 can be coupled with both the implantable device 204 and the targeting device 208. The attachment mechanism 206 can support the targeting device 208 as further illustrated herein. The attachment mechanism 206 can be a separate component from the implantable device 204 and/or the targeting device 208 or can be integral (e.g., part of) with one or both of the implantable device 204 and/or the targeting device 208, for example. The attachment mechanism 206 can be configured to support and/or position the targeting device 208 as further discussed herein. Although the attachment mechanism 206 can be the sole support for the targeting device 208, according to some examples further features such as pins, bone screws and/or additional mounting mechanisms can be utilized to aid the attachment mechanism 206.

As shown in FIG. 2, at step 216 of the method 202, the targeting device 208 can be configured to reference a distal anatomy of the leg 102, in particular a lateral side 218 of a malleoli 220. At step 222 of the method 202, the targeting device 208 can be repositioned and is configured to reference a medial side 224 of the malleoli 220. The order of the steps 216 and 222 can be reversed and need not be performed in the sequence illustrated. According to further techniques, the method 202 can reference other distal anatomic features of the leg (e.g., an estimated or measured middle of the malleoli (such as a midpoint between the ankle alveoli), a fibular notch, a syndesmosis joint, an inferior articular surface, anterior surface, posterior surface, medial border, *Incisura fibularis*, malleolar groove, etc.) or other bone.

The targeting device 208 can include or can produce a visual alignment guide configured to reference distal anatomy of the leg 102 such as the lateral side 218 and the medial side 224 of the malleoli 220. The visual alignment guide can be an alignment mechanism such as a rod, member, concentrated light, or other feature or component. The example of FIG. 2 shows the targeting device 208 configured to generate a laser beam 226 that is directed to the lateral side 218 and the medial side 224. For example, the targeting device 208 is a rangefinder that can determine the distance of an object. Although a single targeting device 208 is shown in FIG. 2, it is contemplated that two (or more) targeting devices could be utilized including a first targeting device dedicated to referencing the lateral side 218 of the malleoli 220 and a second targeting device dedicated to referencing the medial side 224 of the malleoli 220.

As will be discussed in further detail subsequently, the targeting device 208 can include one or more sensors 228. The one or more sensors 228 can include an accelerometer, gyroscope, compass, electronic tilt sensor or other type of sensor capable of measuring second data. This second data can be transmitted to the controller 214. The controller 214 can intraoperatively receive the second data from the targeting device 208. This second data can include, but is not limited to, information about a position of the targeting device 208 such as an angulation of the targeting device 208 while referencing both the lateral side 218 and the medial side 224 of the malleoli 220. The second data includes information regarding the angle of the targeting device 208 along with the geometric data regarding the attachment mechanism 206 (which has a known length) that can be utilized (e.g., compared to the first data) by the system 200 and method 202. This combination of information can allow for a determination of the position of the targeting device 208 relative to the implantable device 204. As the implantable device 204 approximates the position of the medullary canal 210, which is located along the mechanical axis of the tibia 106, the relative position of the targeting device 208 relative to one point along the mechanical axis of the tibia 106 can be determined.

Put another way, the second data collected by the one or more sensors 228 of the targeting device 208 can provide orientation data to the system 200. This orientation data permits the CAS system 200 to determine the orientation in space of the targeting device 208 independently from the orientation provided by the first data collected by the one or more sensors 212 of the implantable device 204. Once the respective orientations of the implantable device 204 and the targeting device 208 are determined, the system 200 can then calculate the difference between the detected orientations of the sensors 228 and 212. This calculated difference in orientation between the two sensors 228 and 212 corresponds to an angle of the mechanical axis 118, which is thus determined by the system 200.

The system 200 and method 202 contemplate alternative techniques for determining the position of the targeting device 208. For example, the one or more sensors 228 of the targeting device 208 could be configured to communicate with the one or more sensors 212 of the implantable device 204. Such communication between the one or more sensors 212 and 228 could provide data regarding a relative positioning between the targeting device 208 and the implantable device 204, for example. The implantable device 204, the attachment mechanism 206 and the targeting device 208 can be equipped with encoders or like electromechanical devices as another contemplated approach to determine the relative orientation between the implantable device 204 and the targeting device 208.

The first data and the second data can be transferred wirelessly or via a wired connection) to the controller 214. The controller 214 can include one or more processors, microprocessors, microcontrollers, electronic control modules (ECMs), electronic control units (ECUs), programmable logic controller (PLC), or any other suitable means for electronically communicating with the implantable device 204 and/or the targeting device 208. The controller 214 can be configured to operate according to a predetermined algorithm or set of instructions for communicating with implantable device 204 and/or the targeting device 208. Such an algorithm or set of instructions can be stored in a database, can be read into an on-board memory of the controller 214, or preprogrammed onto a storage medium or memory accessible by the controller 214, for example, in the form of a floppy disk, hard drive, optical medium, random access memory (RAM), read-only memory (ROM), or any other suitable computer-readable storage medium commonly used in the art (each referred to as a "database"), which can be in the form of a physical, non-transitory storage medium.

The controller 214 can be in electrical communication or connected to a display (not shown), or the like, and various other components, or multiple smart implants, like implantable device 204 and/or targeting device 208. By way of such connection, the controller 214 can receive data such as the first data pertaining to bone orientation and/or bone movement as captured by the implantable device 204 and/or other data such as the second data pertaining to tool angle, tool relative positioning, etc. In response to such input, the controller 214 can perform various determinations and transmit output signals corresponding to the results of such determinations or corresponding to actions that need to be performed, such as alerting the surgeon, making recommendation to the surgeon, robotically and without surgeon guidance implementing orienting one or more cut guides as appropriate based upon the sensed data, etc.

The controller 214, including a human-machine interface, can include various output devices, such as screens, video displays, monitors and the like that can be used to display information, warnings, data, such as text, numbers, graphics, icons, and the like, regarding the status or data captured by implantable device 204 or other data such as the second data. The controller 214, including the human-machine interface, can additionally include a plurality of input interfaces for receiving information and command signals from various sensors associated with the CAS system, the implantable device 204 and/or other surgical tools such as the targeting device 208 and a plurality of output interfaces for sending control signals to various components of the CAS system including the implantable device 204, cut guide(s), etc. Suitably programmed, the controller 214 can serve many additional similar or wholly disparate tasks/purposes.

The implantable device 204 can include an electronics hub such as a circuit board for electrically and structurally coupling electronic components of the implantable device 204. For example, electronics hub can comprise a silicon wafer or a chip onto which electrical couplings are attached for coupling with other components (e.g., a switch, processor, memory, the one or more sensors 212 and the like). The processor can comprise an integrated circuit that controls operation of components of implantable device 204, such as I/O device, a communication device and the one or more sensors 212, etc. The processor can execute instructions stored in memory to operate components of implantable device 204, such as the one or more sensors 212.

The implantable device 204 can include a memory. This can comprise any suitable storage device, such as nonvolatile memory, magnetic memory, flash memory, volatile memory, programmable read-only memory and the like. The memory can include instructions stored therein for the processor to control operation of implantable device 204. For example, memory can include instructions for operating I/O device, communication device and the one or more sensors 212, as well as coordinating output from implantable device 204 such as to the controller 214. Memory can additionally include reference data for comparing data from the one or more sensors 212.

The communication device can comprise one or more devices for receiving input from an interrogation device (e.g., the controller 214 of FIG. 2) or providing an output to interrogation device via various signals. The communication device can provide a signal to the interrogation device. The interrogation device can thereafter, for example, display on human interface device, such as a video display monitor, an indication of information from the implantable device 204.

The communication device can receive a signal from the interrogation device for storing information on memory or providing information to processor for operating the one or more sensors 212 and other electronics components. In examples, the communication device can communicate using wireless communications signals, such as Bluetooth, WiFi, Zigbee, infrared (IR), near field communication (NFC), 3GPP or other technologies. In examples, the communication device can comprise a wired connection or can include a port for receiving a wire for a wired connection.

The communication device can be used in conjunction with an antenna. A battery can comprise a power source for the onboard electronics including the processor, the one or more sensors 212, etc. The battery can include an electro-chemical cell, such as an alkaline or zinc-manganese battery. In examples, power source can comprise a primary, or non-rechargeable battery, a rechargeable battery or another type of power source.

Figure 3A:
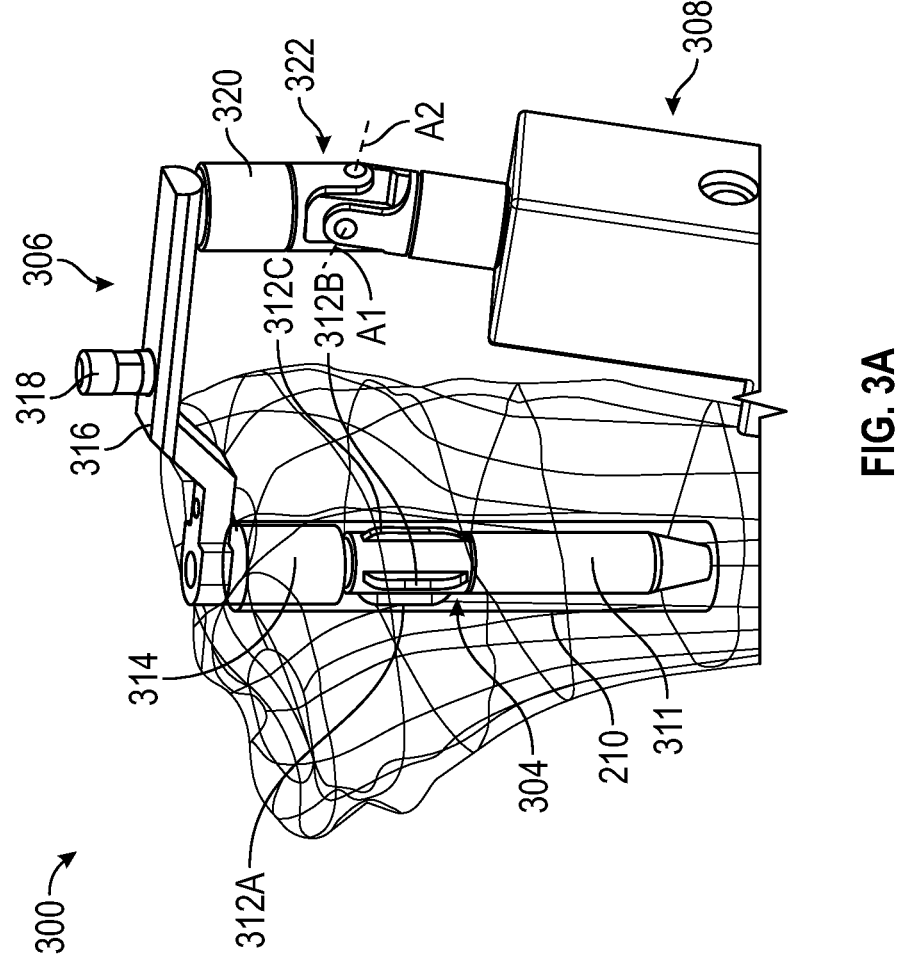
FIGS. 3-3B are different perspective views illustrating an example system including the targeting device, an attachment member and the implantable device in accordance with an example of the present application.
Figure 3:
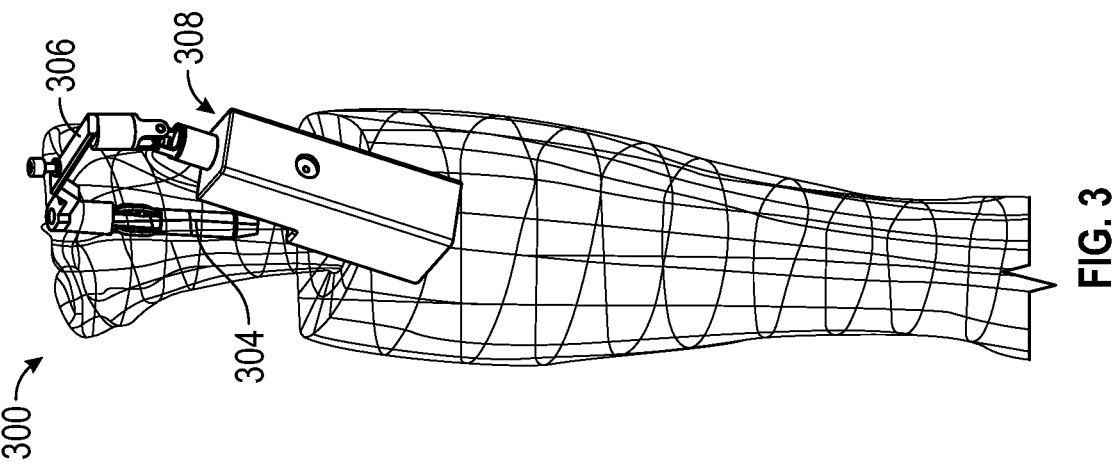
Figure 3B:
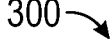
Figure 3B:
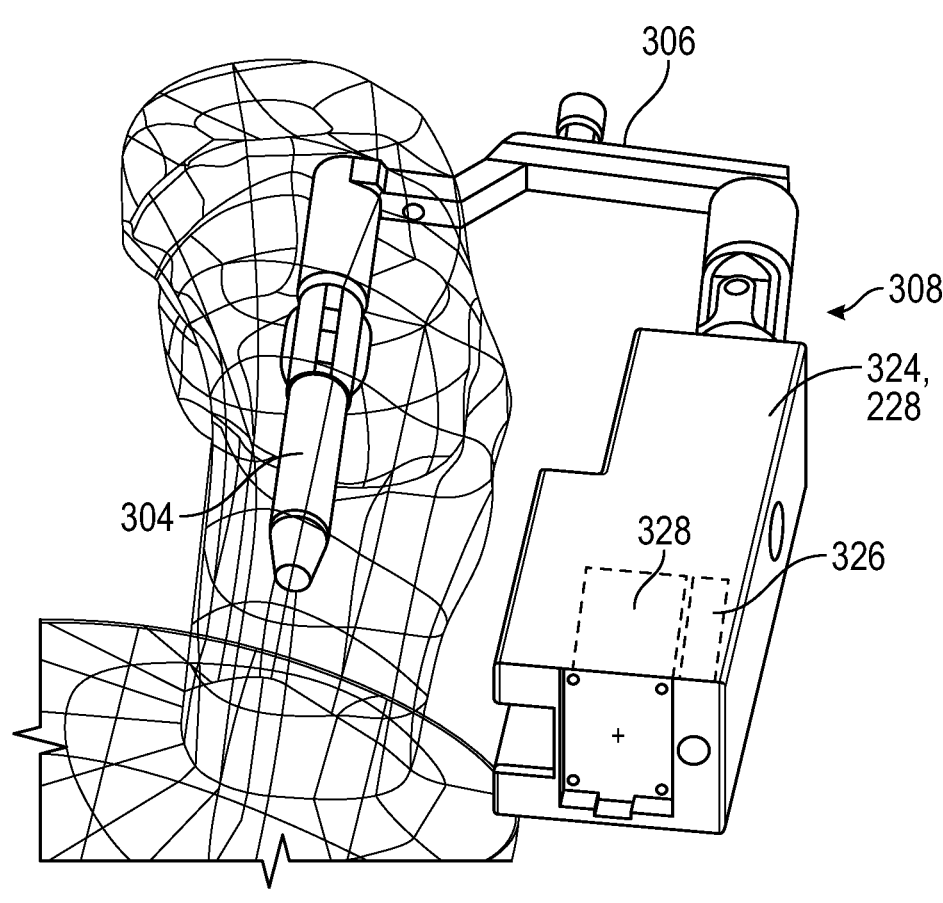

FIGS. 3-3B show a system 300 including examples of an implantable device 304, an attachment mechanism 306 and a targeting device 308. As shown in FIGS. 3-3B, the attachment mechanism 306 can be coupled to the implantable device 304 within the medullary canal 210 (shown in dashed in FIG. 3A) and can further be coupled with the targeting device 308. The attachment mechanism 306 can mount the targeting device 308 for use.

The implantable device 304 can include the one or more sensors 212 (FIG. 2) discussed previously. As shown in FIG. 3A, the implantable device 304 can include a housing 311 and one or more anchoring features 312A, 312B and 312C. The housing 311 can be formed of suitable material (e.g., metal, metal alloy, plastic, etc.) for implantation in the human body. The housing 311 can be generally cylindrical in shape. A diameter of the housing 311 can be between 10 mm and 75 mm, inclusive.

The housing 311 and the one or more anchoring features 312A, 312B and 312C can be sized and shaped as appropriate for insertion into and fixation within the medullary canal 210 of the tibia. Thus, it is contemplated that the housing 311 and the one or more anchoring features 312A, 312B and 312C can be available as a system with different sizes and/or shapes according to some examples. The shape of the housing 311 and the one or more anchoring features 312A, 312B and 312C can be determined based on average medullary canal anatomy derived from three- or two-dimensional scans of the relevant bone using X-Ray, MRI, CT, ultrasound or other imaging techniques. Such shaping can include use of a large number of scans and the ZiBRA™ Anatomical Modeling System to analyze thousands of bones, both male and female, representing a diverse global population, for example. Alternatively, the shape of the housing 311 and the one or more anchoring features 312A, 312B and 312C can be patient-specific (i.e. is constructed specifically for the patient).

The one or more anchoring features 312A, 312B and 312C and/or the housing 311 can have other shapes to fit with other anatomical features, such as a spherical shape, a cylindrical shape, a disk shape, a cup shape and others to mate with other anatomic features of different sized intramedullary canals. As such, a surgeon can select the type of implantable device 304 to use with specific anatomic features or patients.

The one or more anchoring features 312A, 312B and 312C can project outward of the housing 311 and can be configured to engage the surface(s) of the tibia that defines the medullary canal 210 at various locations. Although three anchoring features 312A, 312B and 312C are illustrated, other examples contemplate the use any number of features. Similarly, the relative positioning of the one or more anchoring features 312A, 312B and 312C with respect to one another is purely exemplary.

The one or more anchoring features 312A, 312B and 312C can be any known mechanical feature (e.g., corrugations, porous elements, projections, fins, threads, tangs, prongs, tabs, hooks, loops, arms, apertures (e.g., slot, hole, etc.) or other known mechanical coupling feature) configured for facilitating anchoring to bone. Specifically, the one or more anchoring features 312A, 312B and 312C can be any known mechanical feature configured to anchor with the bone that forms medullary canal 210. The one or more anchoring features 312A, 312B and 312C can be configured as fins in the example of FIGS. 3-3B. The one or more anchoring features 312A, 312B and 312C can be configured to retain the device such that the implantable device 304 does not rotate or otherwise move within the medullary canal 210. It is important for the implantable device 304 to be immobilized to maintain a spatial relationship with other components during surgery such as cut guides, other tools, and/or implants.

Further discussion of the design of the implantable device 304 including the configuration of the housing 311, one or more anchoring features 312A, 312B and 312C and other components thereof can be found in in co-pending IMPLANTABLE SENSOR FOR DETERMINING ORIENTATION AND MOVEMENT OF BONE previously incorporated herein by reference. The one or more anchoring features 312A, 312B and 312C can be rigid having a predefined shape and a fixed orientation that does not change substantially relative to the housing 311 or other components or anatomy. Alternatively, the one or more anchoring features 312A, 312B and 312C can be moveable (e.g., inward toward the housing 311 or outward away from the housing 311) as desired. Furthermore, the one or more anchoring features 312A, 312B and 312C can be configured to flex/deform against and conform with the surface of the bone, for example. Thus, one or more anchoring features 312A, 312B and 312C can be formed of a shape memory or other flexible/conforming material if desired.

As shown in FIG. 3A, one or more anchoring features 312A, 312B and 312C can be chamfered or otherwise shaped for insertion into the medullary canal 210, such as in an insertion direction, and/or in a removal direction, including both directions as shown. The one or more anchoring features 312A, 312B and 312C can project outward a distance from the housing 311. Such region of greatest thickness can extend outward of the housing by between 0.1 mm and 30 mm, inclusive. As shown in FIG. 3A, the one or more anchoring features 312A, 312B and 312C can be configured to engage with the tibia 106 along the medullary canal 210 thereof. The medullary canal 210 can be reamed or otherwise formed in the tibia 106 as known in the art and the implantable device 304 can be inserted down into the medullary canal 310 to the location shown such as with a tool or the attachment mechanism 306. The engagement of the one or more anchoring features 312A, 312B and 312C can retain the implantable device 304 at a desired location along the medullary canal 210 a desired distance distal of an unresected proximal surface of the tibia 106. This distance for the implantable device 204 distal of the unresected proximal surface can be sufficient to allow for one or more resections of a proximal portion of the tibia 106 to remove the unresected proximal surface.

The attachment mechanism 306 can be fixed with respect to the implantable device 304. FIG. 3A further shows the attachment mechanism 306 can include a post 314 configured for insertion into the medullary canal 210. The post 314 can include one or more coupling features (not shown) configured for mechanical attachment with the implantable device 304. The one or more coupling features can be a threaded stud, fastener or any known mechanical feature (e.g., fin, tang, prong, tab, hook, loop, arm, slot, press-fit etc.) configured for coupling with a corresponding feature of the implantable device 304. The post 314 may or may not be in a fixed orientation relative to the implantable device 314.

As shown in FIG. 3A, the attachment mechanism 306 can include an arm 316 extending away from the post 314 and an optional handle 318 extending outward of the arm 316. A distal facing side of the arm 316 can be coupled with a linkage 320 of the targeting device 308. The targeting device 308 at the linkage 320 can include a joint 322. The joint 322 can be configured to allow pivoting movement of a remainder of the targeting device 308 about at least two axes A1 and A2, for example. Thus, the targeting device 308 can be configured to rotate about two or more axes A1 and A2 to orient the targeting device 308 as desired. Rotation of the targeting device 308 about a third axis is also contemplated in some examples. In a variant, there are no more than two rotational degrees of freedom between the targeting device 308 and the implantable device 304, such as about the two axes A1 and A2.

Turning to FIG. 3B, the targeting device 308 can include a main body 324 that can house the one or more sensors 228 discussed previously. The main body 324 can additionally have a laser emitting element 326 configured to producing the laser beam 226 (FIG. 2) and a time of flight sensor 328. The laser emitting element 326 can be in close proximity with the time of flight sensor 328, for example. The time of flight sensor 328 can use infrared light such as the laser beam 226 (or other light) to determine distance information such as a distance to the distal anatomy of the leg 102 (FIG. 2) being targeted by the laser beam 226. More particularly, the time of flight sensor 328 or the laser emitting element 326 can emit a light signal, which hits the targeted anatomy or another object placed in close proximity to the anatomy and returns to the time of flight sensor 328. The time it takes for the laser beam 226 (or other light) to bounce back and be sensed at the time of flight sensor 328 can be measured. From this data, the distance to the target from the targeting device 308 (from the laser emitting element 326 and/or the time of flight sensor 328) can be determined. Any range-finding technology may be used to determine the distance of an object targeted by the targeting device 308.

Figure 4B:
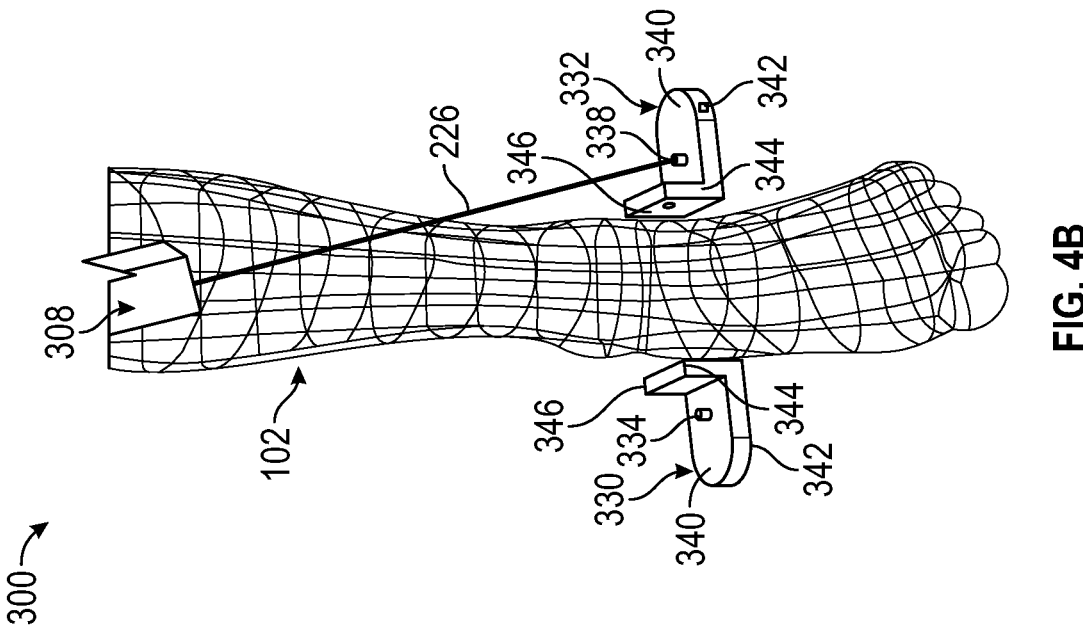
FIGS. 4A and 4B are perspective views of further components of the system of FIGS. 3-3B including target elements being targeted by a laser beam in accordance with an example of the present application.
Figure 4A:
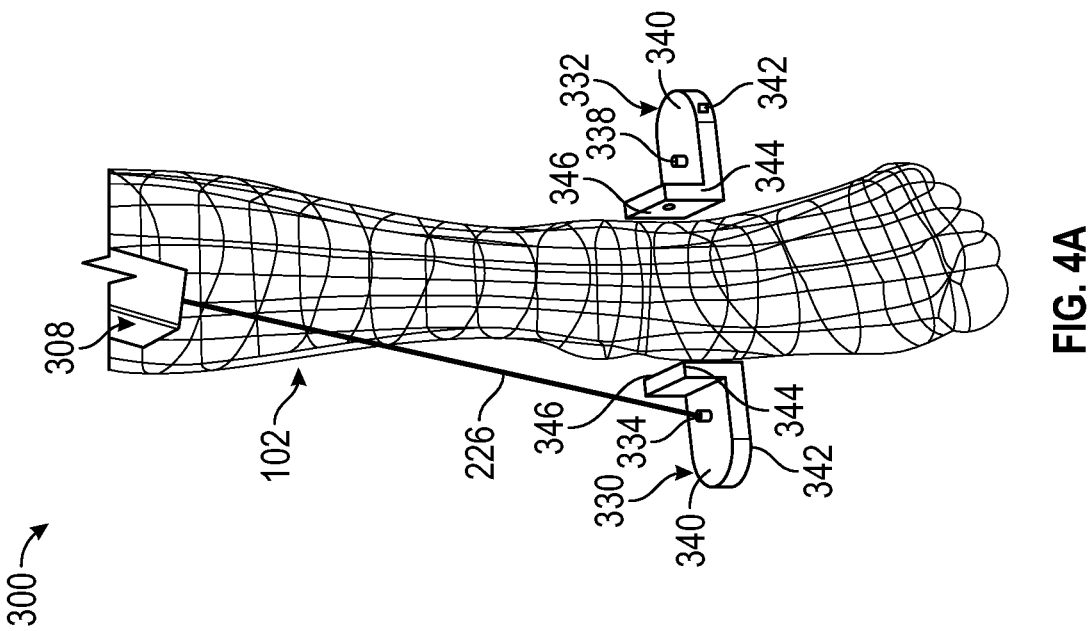

FIGS. 4A and 4B show further components of the system 300 adjacent the distal leg 102 including a first target element 330 and a second target element 332. The first target element 330 can include a first indicia 334 and the second target element 332 can include a second indicia 338. The target elements 330 and 332 are optional.

The first target element 330 and the second target element 332 can be designed as a L-shaped bracket or boss having a substantially flat first major surface 340 and a substantially flat second major surface 342. The second major surface 342 can be opposed from the first major surface 340. The second major surface 342 can be configured to be set on a surface such as a floor, bench, etc. The first major surface 340 can face proximally such as generally facing toward the targeting device 308. The first indicia 334 can extend from or can be positioned on the first major surface 340 of the first target element 330. Similarly, the second indicia 336 can extend from or can be positioned on the first major surface 340 of the second target element 332.

A flange 344 can extend from the first major surface 340 such as generally perpendicularly. The flange 344 can be configured with an exterior surface 346 having a slight arcuate curvature. The flange 344 can be used for alignment of the first target element 330 and the second target element 332 relative to the distal leg 102 of the patient including any one or combination of the foot, ankle, tibia, fibula, etc. As an example, the exterior surface 346 of the flange 344 of each of the first target element 330 and the second target element 332, can be placed in contact with respective ones of a medial side and a lateral side of the ankle. Alternatively, the exterior surface 346 of the flange 344 can be spaced a known distance from the respective ones of the medial side and lateral side of the ankle. Such known distance can place the first target element 330 and the second target element 332 substantially equidistant from the respective one of the medial side and the lateral side.

It should be noted that use of the first target element 330 and the second target element 332 are not contemplated in some examples including the example of FIG. 2. Furthermore, rather than taking the second data from the targeting device 308 at two different orientations, a single orientation for the targeting device 308 such as one that places the laser beam 226 at the middle of the malleoli is contemplated as discussed in U.S. Pat. No. 9,839,533, incorporated by reference above.

FIG. 4A shows the targeting device 308 rotated to a first position with the laser beam 226 placed on the first indicia 334 of the first target element 330. FIG. 4B shows the targeting device 308 rotated to a second position with the laser beam 226 placed on the second indicia 336 of the second target element 332. As discussed previously with regard to FIG. 3B, the distance from the targeting device 308 to the first target element 330 and the second target element 332 can be measured (e.g., by the time of flight sensor). The second data regarding the angulation can also be obtained with the targeting device 308 in the first position of FIG. 4A and the second position of FIG. 4B, relative to the implantable device 304. From such information, the system 300 can determine or have input a middle point of the malleoli. The middle point of the malleoli can correspond to a second position along the mechanical axis of the tibia. From the first position (obtained from the first data of the implantable device 304 (FIG. 3A)) and the second position (corresponding to the middle of the malleoli obtained from the second data in combination with determining time of flight and relative positions of the first target element 330 and the second target element 332), the mechanical axis of the tibia can be fully digitized. Such digitizing information regarding the mechanical axis can include position, angulation and additionally length information as measured from the first position to the second position. Thus, an orientation (including at least two of position, length and angle) of the mechanical axis can be obtained. The implantable device 304 may then serve as a based for a cutting guide to be navigated relative to the mechanical axis. Stated differently, the system may output a tracking of the orientation of the mechanical axis.

Figure 5:
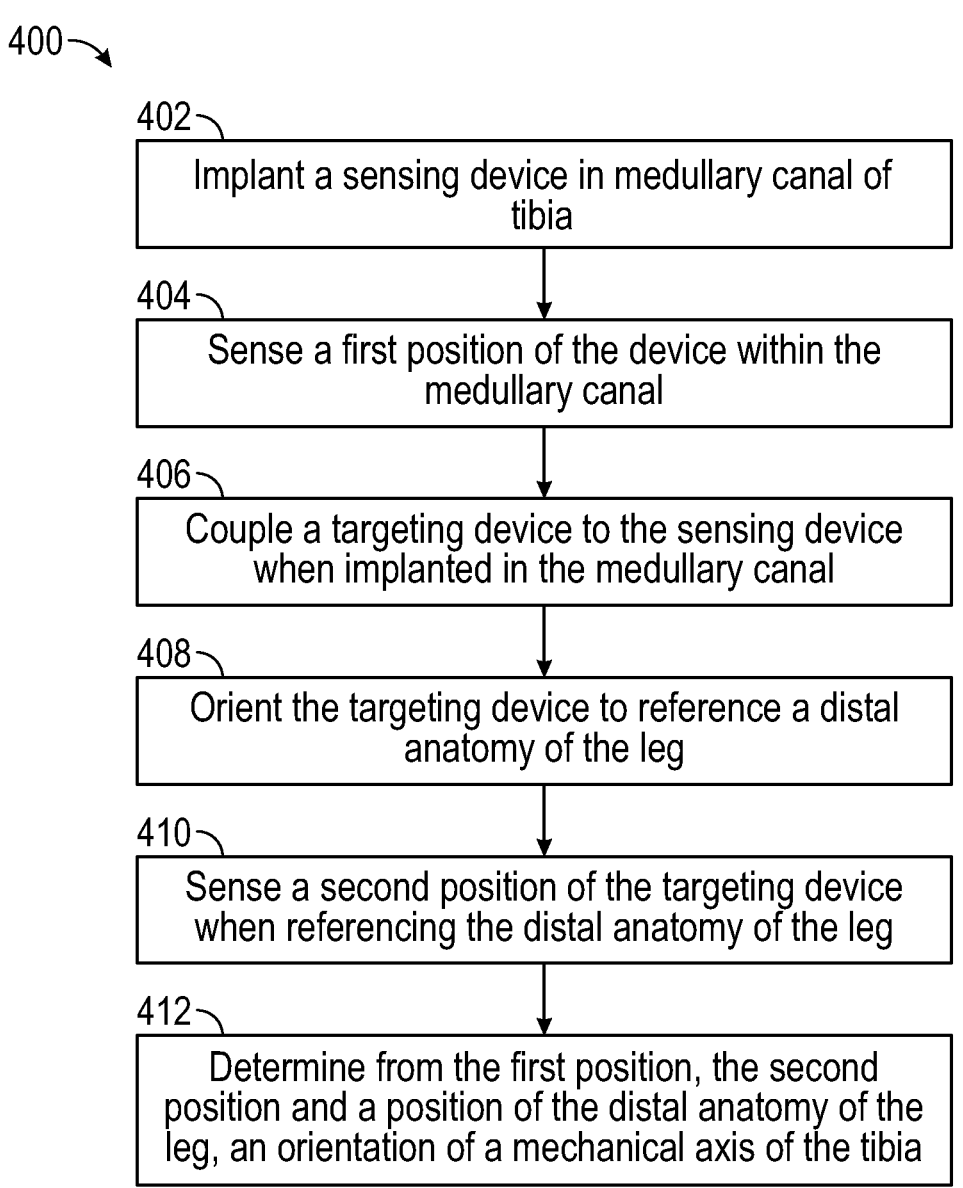
FIG. 5 is a flow diagram of a method of registering a mechanical axis of a tibia for a computer-assisted knee arthroplasty according to an example of the present application.

FIG. 5 shows a flow diagram of a method 400 of digitizing a mechanical axis of the tibia. The method 400 can include implanting a device within a medullary canal of the tibia at step 402. At step 404, the method 400 can include sensing a first position of the device within the medullary canal. The method 400 can include at step 406 coupling a targeting device to the device when implanted within the medullary canal, and calibrating the targeting device for its orientation to be known relative to that of the device within the medullary canal, but this may be optional. Step 408 can include orienting the targeting device to reference a distal anatomy of the leg, in a first orientation of the targeting device. The method 400 can include sensing 410 a second position of the targeting device when referencing the distal anatomy of the leg (based for example on the geometric relation between the attachment mechanism and the targeting device). The method 400 can include determining 412 from the first position, the second position and a position of the distal anatomy of the leg, an orientation (at least a position and orientation) of the mechanical axis of the tibia, now tracked relative to the device in the medullary canal. The distal anatomy of the leg can be a middle of the malleoli, a lateral side of the malleoli, a medial side of the malleoli, combinations thereof or other anatomic features as discussed previously.

The method 400 optionally can include positioning a first target element at or adjacent a lateral side of a malleoli, positioning a second target element at or adjacent a medial side of the malleoli, targeting the first target element with a laser beam while sensing the second position of the targeting device and targeting the second target element with the laser beam while sensing the second position of the targeting device. The laser beam is emitted from the targeting device. The targeting the first element and/or the targeting the second element can include pivoting the targeting device about two or more axes.

According to the method 400, sensing the second position of the targeting device when referencing the distal anatomy of the leg includes determining a position such as an angle of a laser emitting element. The determining from the first position, the second position and the position of the distal anatomy of the leg the orientation of the mechanical axis of the tibia optionally includes determining a time of flight of the laser beam to reach a first target element and a second target element and determining the position corresponding to the middle of the malleoli based upon the position of the laser emitting element of the targeting device and the time of flight of the laser beam.

Figure 6:
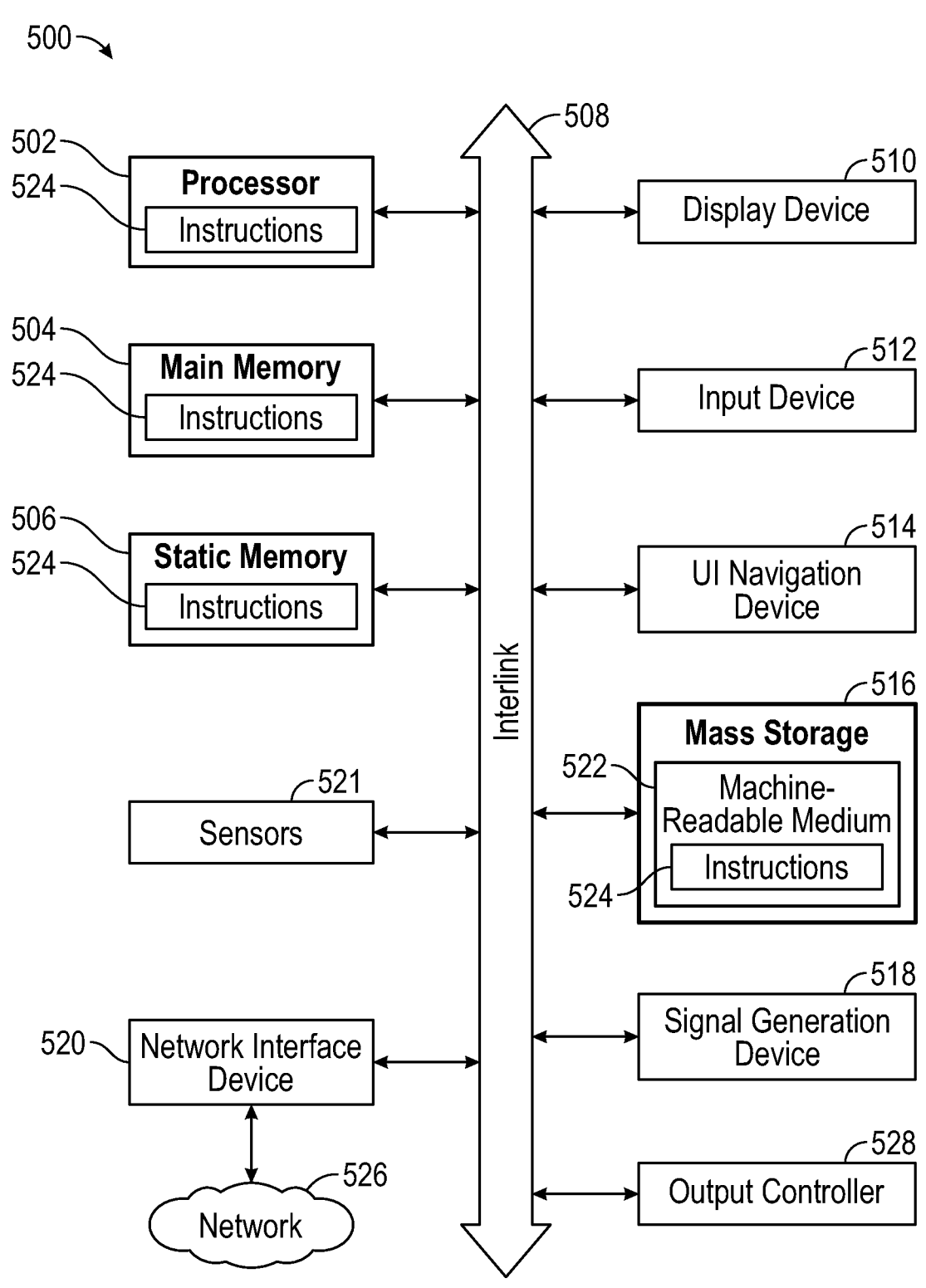
FIG. 6 illustrates a block diagram of an example machine upon which any one or more of the techniques discussed herein may perform in accordance with an example of the present application.

FIG. 6 illustrates a block diagram of an example machine 500 such as the CAS systems discussed previously upon which any one or more of the techniques discussed herein may perform in accordance with some embodiments. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may include a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., CAS system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and sensors 521, such as those of the implantable device, the targeting device, and/or other sensor. The machine 500 may include an output controller 528, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524. The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

The systems, devices and methods discussed in the present application can be useful in efficiently and inexpensively implanting sensing capabilities into a patient in conjunction with a CAS system. As discussed herein, the smart implant can be adapted for use with different anatomies. The smart implant can be temporarily implanted in a patient during trialing such as at the medullary canal of the bone to sense one or more characteristics such as orientation of the bone, movement of the bone, temperature within the medullary canal, pH within the medullary canal, and/or other data.

Claim Related Examples

To further illustrate the apparatuses, systems and methods disclosed herein, the following non-limiting examples (referred to below as aspects and/or techniques) are provided:

In some aspects, the techniques described herein relate to a system for determining an orientation of a mechanical axis of a tibia, the system can optionally include: an implantable device having at least a first sensor configured to collect first data regarding one or more characteristics of a bone of a patient, wherein the implantable device is configured for implantation in a medullary canal of the tibia; an attachment member configured to couple with the implantable device when the implantable device is implanted in the medullary canal of the tibia; and a targeting device moveably coupled to the attachment member, wherein the targeting device is configured to reference a distal anatomy of a leg, and wherein the targeting device has at least a second sensor configured to collect second data regarding at least a position of the targeting device.

In some aspects, the techniques described herein relate to a system, further including at least one target element configured to be placed at or adjacent the distal anatomy of the leg, wherein the targeting device includes or can produce a visual alignment guide configured to reference indicia of the at least one target element.

In some aspects, the techniques described herein relate to a system, wherein the visual alignment guide is a laser emitting element configured to producing a laser beam operable to project onto one or more indicia of the at least one target element.

In some aspects, the techniques described herein relate to a system, wherein the distal anatomy of the leg is a lateral side and a malleoli and a medial side of the malleoli, and wherein the at least one target element includes a first target element configured to reference the lateral side of the malleoli and a second target element configured to reference the medial side of the malleoli.

In some aspects, the techniques described herein relate to a system, wherein the targeting device is configured to pivot about two or more axes to orient the targeting device to have a laser emitting device project the laser beam onto indicia of the first target element and is configured to pivot about the two or more axes to orient the targeting device to have the laser emitting device project the laser beam onto indicia of the second target element.

In some aspects, the techniques described herein relate to a system, wherein the targeting device is moveable to have a laser emitting device project the laser beam onto the first target element and is moveable to have the laser emitting device project the laser beam onto the second target element.

In some aspects, the techniques described herein relate to a system, further including: a controller, communicatively coupled to the first sensor of the implantable device and the second sensor of the targeting device, the controller configured to: determine a first position from the first data; determine an angle of the targeting device; determine a position corresponding to a middle of the malleoli from the second data collected when the laser beam is on the indicia of the first target element and when the laser beam is on the indicia of the second target element; and determine, from the first position, the angle and the position corresponding to the middle of the malleoli, the orientation of the mechanical axis of the tibia.

In some aspects, the techniques described herein relate to a system, wherein controller is configured to determine the position corresponding to the middle of the malleoli from the second data as a function of: compare a position of the laser emitting element of the targeting device relative to the first position to determine the angle of the targeting device; and a time of flight of the laser beam to reach the indicia of the first target element and the indicia of the second target element.

In some aspects, the techniques described herein relate to a method of digitizing a mechanical axis of a tibia for a computer-assisted knee arthroplasty, the method can optionally include: implanting a device within a medullary canal of the tibia; sensing a first position of the device within the medullary canal; coupling a targeting device to the device when implanted within the medullary canal; orienting the targeting device to reference a distal anatomy of a leg; sensing a second position of the targeting device when referencing the distal anatomy of the leg; and determining from the first position, the second position and a position of the distal anatomy of the leg, an orientation of the mechanical axis of the tibia.

In some aspects, the techniques described herein relate to a method, wherein the position of the distal anatomy of the leg is a middle of a malleoli.

In some aspects, the techniques described herein relate to a method, further including: positioning a first target element at or adjacent a lateral side of a malleoli; positioning a second target element at or adjacent a medial side of the malleoli; targeting the first target element with a laser beam while sensing the second position of the targeting device; and targeting the second target element with the laser beam while sensing the second position of the targeting device.

In some aspects, the techniques described herein relate to a method, wherein the laser beam is emitted from the targeting device.

In some aspects, the techniques described herein relate to a method, wherein at least one of targeting the first target element with the laser beam while sensing the second position of the targeting device and targeting the second target element with the laser beam while sensing the second position of the targeting device includes pivoting the targeting device about two or more axes.

In some aspects, the techniques described herein relate to a method, wherein sensing the second position of the targeting device when referencing the distal anatomy of the leg includes determining a position of a laser emitting element.

In some aspects, the techniques described herein relate to a method, wherein the determining from the first position, the second position and the position of the distal anatomy of the leg the orientation of the mechanical axis of the tibia includes: determining a time of flight of the laser beam to reach a first target element and a second target element; and determining the position corresponding to a middle of the malleoli based upon the position of the laser emitting element of the targeting device relative to the device in the medullary canal and the time of flight of the laser beam.

In some aspects, the techniques described herein relate to a system for determining an orientation of a mechanical axis of a tibia, the system optionally can include: an implantable device having at least a first sensor configured to collect first data regarding one or more characteristics of a bone of a patient, wherein the implantable device is configured for implantation in a medullary canal of the tibia; a targeting device configured to moveably relative to the implantable device, wherein the targeting device is configured to reference a distal anatomy of a leg, and wherein the targeting device has at least a second sensor configured to collect second data regarding at least a position of the targeting device; at least one target element configured to be placed at or adjacent the distal anatomy of the leg, wherein the targeting device includes a visual alignment guide configured to reference the at least one target element; and a controller communicatively coupled to the first sensor of the implantable device and the second sensor of the targeting device, the controller configured to: intraoperatively receive first data regarding the position of the implantable device within the medullary canal of the tibia, intraoperatively receive the second data regarding the position of the targeting device while referencing the at least one target element, determine based upon at least the second data a position of the distal anatomy of the leg, determine based upon the first data and the position of the distal anatomy of the leg the orientation of the mechanical axis of the tibia, and output the orientation of the mechanical axis for use during a computer-assisted knee arthroplasty.

In some aspects, the techniques described herein relate to a system, further including an attachment member configured to couple with the implantable device when the implantable device is implanted in the medullary canal of the tibia, and wherein the targeting device is moveably coupled to the targeting device.

In some aspects, the techniques described herein relate to a system, wherein the controller is configured to determine the orientation of the distal anatomy of the leg based upon: comparing the second data, which corresponds to an angle of a laser emitting element that emits a laser beam, relative to the first position; and measuring a time of flight of the laser beam to reach the first target element and the second target element.

In some aspects, the techniques described herein relate to a system, wherein the targeting device is configured to pivot about two or more axes to orient the targeting device to have the laser emitting element project the laser beam as desired.

In some aspects, the techniques described herein relate to a system, wherein the distal anatomy of the leg is a lateral side and a malleoli and a medial side of the malleoli, wherein the at least one target element includes a first target element configured to reference the lateral side of the malleoli and a second target element configured to reference the medial side of the malleoli, and wherein targeting device is moveable to have the laser emitting device project the laser beam onto the first target element and is moveable to have the laser emitting device project the laser beam onto the second target element.

Each of these non-limiting examples can stand on its own, or can be combined in various permutations or combinations with one or more of the other examples. These and other examples and features of the present apparatuses, systems and methods will be set forth in part in the Detailed Description.

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for determining an orientation of a mechanical axis of a tibia, the system comprising:
an implantable device having at least a first sensor configured to collect first data regarding one or more characteristics of a bone of a patient, wherein the implantable device is configured for implantation in a medullary canal of the tibia;
an attachment member configured to couple with the implantable device when the implantable device is implanted in the medullary canal of the tibia;
a targeting device moveably coupled to the attachment member, wherein the targeting device is configured to reference a distal anatomy of a leg, and wherein the targeting device has at least a second sensor configured to collect second data regarding a position and/or orientation of the targeting device; and
at least one target element configured to be placed at or adjacent the distal anatomy of the leg, wherein the targeting device includes or can produce a visual alignment guide configured to reference indicia of the at least one target element, the visual alignment guide being a laser emitting element configured to produce a laser beam operable to project onto one or more indicia of the at least one target element, the at least one target element including a first target element configured to reference a lateral side of a malleoli and a second target element configured to reference a medial side of a malleoli, the targeting device being configured to pivot about two or more axes to orient the targeting device to have the laser emitting element project the laser beam onto the indicia of the first target element and is configured to pivot about the two or more axes to orient the targeting device to have the laser emitting element project the laser beam onto the indicia of the second target element; and
a controller, communicatively coupled to the first sensor of the implantable device and the second sensor of the targeting device, the controller configured to:
determine a first position from the first data,
determine an angle of the targeting device, determine a position corresponding to a middle of the malleoli from the second data collected when the laser beam is on the indicia of the first target element and when the laser beam is on the indicia of the second target element, and
determine, from the first position, the angle and the position corresponding to the middle of the malleoli, the orientation of the mechanical axis of the tibia.

2. The system of claim 1, wherein the controller is configured to determine the position corresponding to the middle of the malleoli from the second data as a function of:
compare a position and/or orientation of the laser emitting element of the targeting device relative to the first position to determine the angle of the targeting device; and
a time of flight of the laser beam to reach the indicia of the first target element and the indicia of the second target element.

3. A method of digitizing a mechanical axis of a tibia for a computer-assisted knee arthroplasty, the method comprising:
implanting a device within a medullary canal of the tibia;
recording a first position of the device within the medullary canal;
coupling a targeting device to the device when implanted within the medullary canal;
orienting the targeting device to reference a distal anatomy of a leg;
sensing a second position of the targeting device when referencing the distal anatomy of the leg; and
determining from the first position, the second position and a position of the distal anatomy of the leg, an orientation of the mechanical axis of the tibia, and outputting a tracking of the orientation of the mechanical axis.

4. The method of claim 3, wherein the position of the distal anatomy of the leg is a middle of a malleoli.

5. The method of claim 3, further comprising:
positioning a first target element at or adjacent a lateral side of a malleoli;
positioning a second target element at or adjacent a medial side of the malleoli;
targeting the first target element with a laser beam while sensing the second position of the targeting device; and
targeting the second target element with the laser beam while sensing the second position of the targeting device.

6. The method of claim 5, wherein the laser beam is emitted from the targeting device.

7. The method of claim 5, wherein at least one of targeting the first target element with the laser beam while sensing the second position of the targeting device and targeting the second target element with the laser beam while sensing the second position of the targeting device includes pivoting the targeting device about two or more axes.

8. The method of claim 6, wherein sensing the second position of the targeting device when referencing the distal anatomy of the leg includes determining a position of a laser emitting element.

9. The method of claim 8, wherein the determining from the first position, the second position and the position of the distal anatomy of the leg the orientation of the mechanical axis of the tibia includes:
determining a time of flight of the laser beam to reach a first target element and a second target element; and
determining the position corresponding to a middle of the malleoli based upon the position of the laser emitting element of the targeting device relative to the device in the medullary canal and the time of flight of the laser beam.

10. A system for determining an orientation of a mechanical axis of a tibia, the system comprising:

an implantable device having at least a first sensor configured to collect first data regarding one or more characteristics of a bone of a patient, wherein the implantable device is configured for implantation in a medullary canal of the tibia;

a targeting device configured to moveably relative to the implantable device, wherein the targeting device is configured to reference a distal anatomy of a leg, and wherein the targeting device has at least a second sensor configured to collect second data regarding at least a position of the targeting device;

at least one target element configured to be placed at or adjacent the distal anatomy of the leg, wherein the targeting device includes a visual alignment guide configured to reference the at least one target element; and a controller communicatively coupled to the first sensor of the implantable device and the second sensor of the targeting device, the controller configured to:

intraoperatively receive first data regarding the position of the implantable device within the medullary canal of the tibia, intraoperatively receive the second data regarding the position of the targeting device while referencing the at least one target element, determine based upon at least the second data a position of the distal anatomy of the leg, determine based upon the first data and the position of the distal anatomy of the leg the orientation of the mechanical axis of the tibia, and output the orientation of the mechanical axis for use during a computer-assisted knee arthroplasty.

11. The system of claim 10, further comprising an attachment member configured to couple with the implantable device when the implantable device is implanted in the medullary canal of the tibia, and wherein the targeting device is moveably coupled to the targeting device.

12. The system of claim 10, wherein the controller is configured to determine the orientation of the distal anatomy of the leg based upon:

comparing the second data, which corresponds to an angle of a laser emitting element that emits a laser beam, relative to the first position; and measuring a time of flight of the laser beam to reach the first target element and the second target element.

13. The system of claim 12, wherein the targeting device is configured to pivot about two or more axes to orient the targeting device to have the laser emitting element project the laser beam as desired.

14. The system of claim 13, wherein the distal anatomy of the leg is a lateral side and a malleoli and a medial side of the malleoli, wherein the at least one target element includes a first target element configured to reference the lateral side of the malleoli and a second target element configured to reference the medial side of the malleoli, and wherein targeting device is moveable to have the laser emitting device project the laser beam onto the first target element and is moveable to have the laser emitting device project the laser beam onto the second target element.

* * * * *